(12) United States Patent
Heo et al.

(10) Patent No.: US 10,312,292 B2
(45) Date of Patent: Jun. 4, 2019

(54) X-RAY DETECTOR

(71) Applicants: Rayence Co., Ltd., Gyeonggi-do (KR); VATECH EWOO Holdings Co., Ltd., Gyeonggi-do (KR)

(72) Inventors: Sung Kyn Heo, Gyeonggi-do (KR); Dong Hui Shin, Gyeonggi-do (KR); Tae Woo Kim, Gyeonggi-do (KR); Min Seok Yun, Gyeonggi-do (KR)

(73) Assignees: Rayence Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 0 days.

(21) Appl. No.: 15/757,994

(22) PCT Filed: Sep. 7, 2016

(86) PCT No.: PCT/KR2016/010041
§ 371 (c)(1),
(2) Date: Mar. 7, 2018

(87) PCT Pub. No.: WO2017/043871
PCT Pub. Date: Mar. 16, 2017

(65) Prior Publication Data
US 2018/0240848 A1  Aug. 23, 2018

(30) Foreign Application Priority Data

Sep. 7, 2015 (KR) .......... 10-2015-0126401
May 4, 2016 (KR) .......... 10-2016-0055463
May 4, 2016 (KR) .......... 10-2016-0055518

(51) Int. Cl.
*H01L 27/30* (2006.01)
*G01T 1/24* (2006.01)
(Continued)

(52) U.S. Cl.
CPC ............ *H01L 27/308* (2013.01); *A61B 6/032* (2013.01); *A61B 6/145* (2013.01); *A61B 6/502* (2013.01);
(Continued)

(58) Field of Classification Search
CPC ............................. H01L 27/308; A61B 6/032
See application file for complete search history.

(56) References Cited

U.S. PATENT DOCUMENTS

2005/0161604 A1  7/2005  Baniecki et al.
2012/0181516 A1  7/2012  Sekiguchi et al.
(Continued)

FOREIGN PATENT DOCUMENTS

KR         10-1366122 B1    2/2014
KR      10-2015-0056851 A   5/2015
(Continued)

OTHER PUBLICATIONS

Yakunin et al. "Detection of X-ray photons by solution-processed organicinorganic perovskites", Nat Photonics. Jul. 2015 ; 9(7): 444-449.*

*Primary Examiner* — Michael C Bryant
(74) *Attorney, Agent, or Firm* — IP Legal Services, LLC

(57) ABSTRACT

Disclosed is a direct-conversion-type X-ray detector, including a first electrode on a substrate, a semiconductor structure including a photoconductor using a perovskite material on the first electrode, and a second electrode on the semiconductor structure.

16 Claims, 8 Drawing Sheets

(51) Int. Cl.

| | | |
|---|---|---|
| *A61B 6/14* | (2006.01) | |
| *A61B 6/00* | (2006.01) | |
| *C09K 11/66* | (2006.01) | |
| *C09K 11/88* | (2006.01) | |
| *C09J 133/14* | (2006.01) | |
| *G01T 1/20* | (2006.01) | |
| *H01L 51/42* | (2006.01) | |
| *H01L 51/44* | (2006.01) | |
| *H01G 9/20* | (2006.01) | |
| *H01L 51/00* | (2006.01) | |
| *A61B 6/03* | (2006.01) | |

(52) U.S. Cl.
CPC ........... *C09J 133/14* (2013.01); *C09K 11/661* (2013.01); *C09K 11/664* (2013.01); *C09K 11/88* (2013.01); *G01T 1/2018* (2013.01); *G01T 1/24* (2013.01); *H01G 9/2018* (2013.01); *H01L 51/0077* (2013.01); *H01L 51/426* (2013.01); *H01L 51/4213* (2013.01); *H01L 51/4293* (2013.01); *H01L 51/441* (2013.01); *A61B 6/14* (2013.01); *A61B 6/4233* (2013.01); *H01L 51/448* (2013.01)

(56) References Cited

U.S. PATENT DOCUMENTS

| | | |
|---|---|---|
| 2015/0249170 A1 | 9/2015 | Snaith et al. |
| 2016/0268510 A1* | 9/2016 | Moon .................. H01L 51/424 |
| 2016/0285021 A1 | 9/2016 | Yang et al. |

FOREIGN PATENT DOCUMENTS

| | | |
|---|---|---|
| KR | 10-1546500 B1 | 8/2015 |
| WO | 2015/116297 A2 | 8/2015 |

* cited by examiner

X-RAY DETECTOR

CROSS REFERENCE TO RELATED APPLICATIONS

This application is a National Stage Patent Application of PCT International Patent Application No. PCT/KR2016/010041 (filed on Sep. 7, 2016) under 35 U.S.C. § 371, which claims priority to Korean Patent Application Nos. 10-2015-0126401 (filed on Sep. 7, 2015), 10-2016-0055463 (filed on May 4, 2016), and 10-2016-0055518 (filed on May 4, 2016), the teachings of which are incorporated herein in their entireties by reference.

TECHNICAL FIELD

The present invention relates to an X-ray detector, and more particularly to an X-ray detector using a perovskite material.

BACKGROUND ART

Digital X-ray detectors are classified into indirect-conversion-type X-ray detectors and direct-conversion-type X-ray detectors.

In indirect-conversion-type X-ray detectors, X-rays are converted into visible light using a scintillator, the visible light is converted into an electrical signal using a photodiode, and the electrical signal is detected. Meanwhile, in direct-conversion-type X-ray detectors, a photoconductor for directly generating an electrical signal through absorption of X-rays is used.

In this way, a direct-conversion-type detector is able to detect an electrical signal directly converted from X-rays, thus exhibiting high resolution, conversion efficiency and collection efficiency to thereby reduce radiation poisoning, but is currently problematic because of difficulty in commercialization.

In this regard, a photoconductor used for the direct-conversion-type detector needs to satisfy various properties, and photoconductors proposed to date, such as a-Se, CdTe, $HgI_2$, $PbI_2$ and PbO, have many defects.

a-Se suffers from high application voltage, low sensitivity and a charge-trapping phenomenon, and thus the use thereof as a photoconductor is limited.

Furthermore, CdTe, $HgI_2$, $PbI_2$ and PbO are disadvantageous because of complicated processing and high price, make it difficult to manufacture a large-area detector, and require a long period of time to realize mass production, and techniques for reproducible fabrication are currently insufficient.

Thus, there is an urgent need for a photoconductor that enables the mass production of detectors at low cost while satisfying diverse properties required of the photoconductor, in addition to the materials developed to date.

DISCLOSURE

Technical Problem

Accordingly, the present invention is intended to provide a direct-conversion-type X-ray detector using a photoconductor that enables the mass production of detectors at low cost while satisfying the diverse properties required of the photoconductor.

In addition, the present invention is intended to provide a technique that enables deposition without adhesive problems even on CMOS and flexible plastic substrates, in addition to existing transparent conductive electrodes (ITO, SnO)/glass substrate.

Technical Solution

Therefore, the present invention provides a direct-conversion-type X-ray detector, comprising: a first electrode on a substrate; a semiconductor structure including a photoconductor using a perovskite material on the first electrode; and a second electrode on the semiconductor structure.

The perovskite material may be represented by the chemical formula ABX3, A being Cs, methyl ammonium ($CH_3NH_3$), or formamidinium ($NH_2CH=NH_2$), B being Pb, Sn, Cu, Ni, Bi, Co, Fe, Mn, Cr, Cd, Ge, or Yb, and X being $I_xBr_{(1-x)}$, $I_xCl_{(1-x)}$, or $Br_xCl_{(1-x)}$ ($0.2 \leq x \leq 1$, a real number).

The semiconductor structure may include a hole transport layer and an electron transport layer, and the photoconductor may be provided in a film form between the hole transport layer and the electron transport layer.

The hole transport layer may include first and second hole transport layers.

The semiconductor structure may include one of an electron transport layer and a hole transport layer, with a photoconductor film having a type opposite thereto and configured such that the photoconductor is provided in a film form, or may include an electron transport layer and a hole transport layer, and when the semiconductor structure includes the electron transport layer and the hole transport layer, the photoconductor may be provided in the form of particles inside one of the electron transport layer and the hole transport layer.

The semiconductor structure may include a hole transport layer and an electron transport layer, with a photoconductor film having a P type disposed therebetween and configured such that the photoconductor is provided in a film form, or may include a hole transport layer and an electron transport layer, with an additional hole transport layer disposed therebetween and configured such that the photoconductor is provided in the form of particles therein.

The substrate may be a CMOS substrate or a plastic substrate, and an adhesive polymer formed between the first electrode and the photoconductor may be further included.

The adhesive polymer may be PAP (polyacryloyl piperidine).

The X-ray detector may further comprise a sealing member configured to seal the entire stacking structure comprising the substrate, the first electrode, the semiconductor structure and the second electrode, or to seal the entire stacking structure comprising the substrate, the first electrode and the semiconductor structure.

The sealing member may be formed of any one or a mixture of at least two selected from among a polyethylene-based resin, a polypropylene-based resin, a cyclic polyolefin-based resin, a polystyrene-based resin, an acrylonitrile-styrene copolymer, an acrylonitrile-butadiene-styrene copolymer, a poly(vinyl chloride)-based resin, a fluorine-based resin, a poly(meth)acrylate-based resin, and a polycarbonate-based resin, or may be formed of Parylene.

The photoconductor film may have a thickness of 200 μm~800 μm when the X-detector is used for a dental CT or cephalo sensor, a thickness of 150 μm~600 μm when the X-detector is used for a dental panorama sensor, a thickness of 100 μm~450 μm when the X-detector is used for an intraoral (I/O) sensor, a thickness of 60 μm~300 μm when the X-detector is used for a mammography sensor, and a thickness of 90 μm~1000 μm when the X-detector is used for a medical fluoroscopy X-ray sensor.

The semiconductor structure may include a photoconductor film using the perovskite material and a quantum dot material for converting incident X-rays into visible light.

The quantum dot may be formed of a-Se, Cs, CdSe, CdS, PbO, or $PbI_2$, and may have a diameter of 1 nm~100 nm.

The quantum dot may be provided in the form of being dispersed in the photoconductor film, or in the form of a film in contact with at least one of the upper surface and the lower surface of the photoconductor film.

The semiconductor structure may include one of a hole transport layer and an electron transport layer, and one of the hole transport layer and the electron transport layer may be disposed between one of the first and second electrodes and the photoconductor film configured such that the quantum dot is provided therein or thereon.

The semiconductor structure may include a hole transport layer and an electron transport layer, the hole transport layer may be disposed between one of the first and second electrodes and the photoconductor film configured such that the quantum dot is provided therein or thereon, and the electron transport layer may be disposed between the remaining one of the first and second electrodes and the photoconductor film configured such that the quantum dot is provided therein or thereon.

The film comprising the quantum dot may have a thickness of 100 nm~1000 μm.

Advantageous Effects

According to the present invention, a perovskite material has properties suitable for use as a photoconductor for an X-ray detector, and moreover, is inexpensive, can exhibit superior deposition properties on a substrate, and is easy to manufacture. Thereby, mass production of an X-ray detector at low cost within a short processing time can become possible.

In addition to the perovskite material, a quantum dot material for converting X-rays having specific energy into visible light is used, thus absorbing X-rays in a wide energy range from substantially low energy to high energy, thereby minimizing the dose of radiation poisoning to a patient and obtaining an image having high resolution and low noise.

MODE FOR INVENTION

Figure 1:
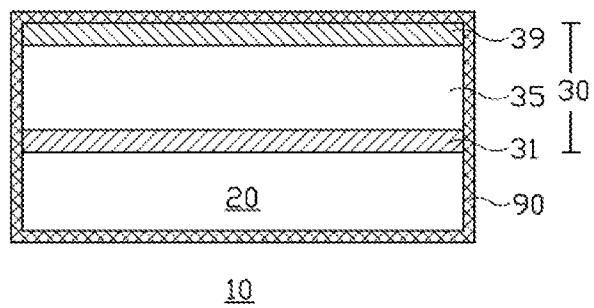
FIGS. 1 to 10 are cross-sectional views schematically showing various structures of an X-ray detector using a perovskite material according to a first embodiment of the present invention.

Hereinafter, a detailed description will be given of embodiments of the present invention with reference to the appended drawings.

First Embodiment

A direct-conversion-type X-ray detector according to a first embodiment of the present invention includes a perovskite material serving as a photoconductor.

Perovskite, having a crystal structure represented by the chemical formula ABX3, is known to be a special material that exhibits the properties of all of a non-conductor, a semiconductor, a conductor, and even a superconductor. In this embodiment, such a perovskite material is used as the photoconductor.

Here, the perovskite material used in the present embodiment is specified, and materials that constitute ABX3 are as follows.

A: an organic material, examples of which include methyl ammonium ($CH_3NH_3$) and formamidinium ($NH_2CH=NH_2$), or an inorganic material, an example of which includes cesium (Cs);

B: a metal material, examples of which include divalent transition metals, such as Pb, Sn, Cu, Ni, Bi, Co, Fe, Mn, Cr, Cd, Ge, Yb, and the like;

X: a halogen material, examples of which include $I_x Br_{(1-x)}$, $I_x Cl_{(1-x)}$, and $Br_x Cl_{(1-x)}$ ($0.2 \leq x \leq 1$, a real number).

In the present embodiment, when the perovskite material having the above structure is used, a photoconductor having superior properties may be obtained.

Here, among the examples of the B material that is listed above, Pb, Bi and Cd are more preferably used than the other materials.

Below is a description of the perovskite material using an organic material as the A material.

[Table 1] below shows the properties of $(CH_3NH_3)PbI_3$, which is an example of the perovskite material using an organic material as the A material, and of existing proposed materials.

With reference thereto, the perovskite material of the present embodiment has a high atomic number, low energy band gap and low ionization energy, and may exhibit increased quantum efficiency due to the small trap density. It has higher mobility properties than a-Se, which is currently widely used for direct-conversion-type detectors.

TABLE 1

|  | Photoconductor | | | | | |
| --- | --- | --- | --- | --- | --- | --- |
|  | a-Se | CdTe | Poly-$HgI_2$ | Poly-$PbI_2$ | Poly-PbO | Poly-$(CH_3NH_3)PbI_3$ |
| Atomic number (Z) | 34 | 48/62 | 80/53 | 82/53 | 82/8 | 82/53 |
| Energy band gap (eV) | 2.2 | 1.44 | 2.1 | 2.4 | 1.9 | 1.55 |
| Density (g/cm$^3$) | 4.3 | 5.85 | 6.36 | 6.16 | 9.6 | 4.28 |
| Trap density (cm$^{-3}$) | $10^{16}$ | $10^{13}$~$10^{14}$ | ~$10^{13}$ | ~$10^{13}$ | — | ~$10^{10}$ |
| Ionization energy (W±) | 45 | 5 | 5 | 5 | 8 | <5 |

TABLE 1-continued

| | | Photoconductor | | | | | |
|---|---|---|---|---|---|---|---|
| | | a-Se | CdTe | Poly-HgI$_2$ | Poly-PbI$_2$ | Poly-PbO | Poly-(CH$_3$NH$_3$)PbI$_3$ |
| Mobility (cm$^2$/Vs) | Electron | ~10$^{-3}$ | 10$^3$ | 10$^2$ | — | 50 | ~6 |
| | Hole | ~10$^{-2}$ | ~90 | 4 | 0.01~0.1 | — | 19 |
| Resistivity (Ω) | | 10$^{14}$~10$^{15}$ | 10$^9$ | ~10$^{13}$ | 10$^{11}$~10$^{12}$ | ~10$^{12}$ | 10$^7$ |

As mentioned above, the perovskite material of the present embodiment may sufficiently satisfy requirements through the preparation of CH$_3$NH$_3$Pb(I$_x$Br$_{1-x}$)$_3$.

Furthermore, the perovskite material using the organic material as the A material is inexpensive compared to existing materials, and may be easily formed through synthesis of organic or inorganic materials, and thus enables the mass production of a large-area detector at low cost within a short time.

The perovskite material using the organic material as the A material may exhibit superior deposition ability on a substrate compared to existing materials, to thus improve interfacial characteristics with a CMOS substrate or the like, thereby improving detection efficiency of the detector.

In the perovskite material using the organic material as the A material, the crystal size of perovskite is determined depending on the concentration. Specifically, the crystal size decreases with an increase in the concentration of the organic material, and increases with a decrease in the concentration of the organic material. Also, the crystal size is related to the amount of absorption of X-rays, and specifically the amount of absorption of X-rays is increased with a decrease in the crystal size. Based on the results of measurement of light absorbance through the control of the concentration of the organic material, light absorbance becomes optimized when the concentration of the organic material is 35 mM~45 mM, and preferably 38 mM, as in solar light.

The perovskite material, which is used as the photoconductor for a direct-conversion-type X-ray detector, has to be formed into a relatively thick film having a predetermined thickness or more taking into consideration the X-ray absorption properties, and is preferably provided in the form of a film having a thickness ranging from 100 μm to at least 1 mm.

Such a photoconductor may be manufactured using a spray-coating process, a sol-gel-coating process, a spin-coating process, a slot-die-coating process, a thermal deposition process, a sequential vapor deposition process, a vapor-assisted solution process, etc.

Among these, a spray-coating process, a sol-gel-coating process, a vapor deposition process or a vapor-assisted solution process is preferably performed.

As such, the vapor deposition process may be performed in various manners, and, for example, may be a thermal deposition process. The thermal deposition process is able to form a uniform thick film having good quality compared to the other deposition processes, and impurity doping in the air may be maximally suppressed.

Hereinafter, various examples of the X-ray detector using the perovskite material as the photoconductor according to the present embodiment are described with reference to the drawings.

FIGS. 1 to 10 are cross-sectional views schematically showing various structures of an X-ray detector using a perovskite material according to a first embodiment of the present invention.

Figure 2:
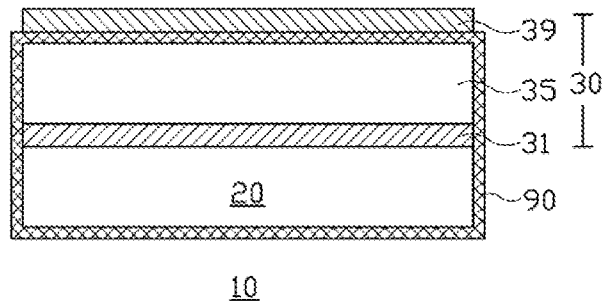

The X-ray detector 10 of FIGS. 1 and 2 includes a photoelectric element 30 having a Schottky structure on a substrate 20.

The substrate 20 includes a plurality of detection pixels for reading an electric signal generated from the photoelectric element. The substrate 20 may be provided in various forms, and examples thereof may include a CMOS substrate, a glass substrate, a plastic substrate having flexible properties, etc. Here, examples of the plastic substrate may include polyethylene terephthalate (PET), polyethylene naphthalate (PEN), polyimide (PI), polycarbonate (PC), polypropylene (PP), triacetyl cellulose (TAC), and polyether sulfone (PES).

The photoelectric element 30 includes a first electrode 31, which is the lower electrode formed on the substrate 20, a second electrode 39, which is the upper electrode formed on the first electrode 31, and a semiconductor structure disposed between the first and second electrodes 31, 39 to perform a photoelectric function, the semiconductor structure being composed of a photoconductor film 35.

The photoconductor film 35 is formed of a perovskite material. One of the first and second electrodes 31, 39 corresponds to a cathode, and the remaining one corresponds to an anode.

The material for forming the first and second electrodes 31, 39 may include, for example, any one or a mixture of at least two selected from among ITO, F—SnO, gold, silver, platinum, palladium, copper, aluminum, carbon, cobalt sulfide, copper sulfide, and nickel oxide, or alternatively may include an inorganic conductive electrode material, such as single or multiple carbon nanotubes or graphene, an organic conductive electrode material such as PEDOT:PSS, or a nanowire electrode material such as a silver nanowire (Ag Nanowire) metal material.

Also, an adhesive polymer may be provided between the first electrode 31 and the perovskite photoconductor film 35, and the adhesive polymer may be formed with PAP (polyacryloyl piperidine).

Here, the photoconductor film 35 has low resistance to external moisture or oxygen. In order to protect the photoconductor film 35 from the outside, the X-ray detector 10 includes a sealing member 90.

In this regard, for example, the X-ray detector 10 of FIG. 1 is configured such that the sealing member 90 is provided so as to seal the entire stacking structure comprising the substrate 20 and the photoelectric element 30 from the outside.

In another example, the X-ray detector 10 of FIG. 2 is configured such that the sealing member 90 is provided so as to seal the entire stacking structure comprising the substrate 20 and the construction (i.e. the first electrode 31 and the semiconductor layer of the photoconductor film 35) of the photoelectric element 30, other than the second electrode 39.

The material for forming the sealing member 90 may include, for example, any one or a mixture of at least two selected from among a polyethylene-based resin, a polypropylene-based resin, a cyclic polyolefin-based resin, a polystyrene-based resin, an acrylonitrile-styrene copolymer, an acrylonitrile-butadiene-styrene copolymer, a poly(vinyl chloride)-based resin, a fluorine-based resin, a poly(meth) acrylate-based resin, and a polycarbonate-based resin, or may include Parylene. Here, Parylene is preferably used.

Figure 3:
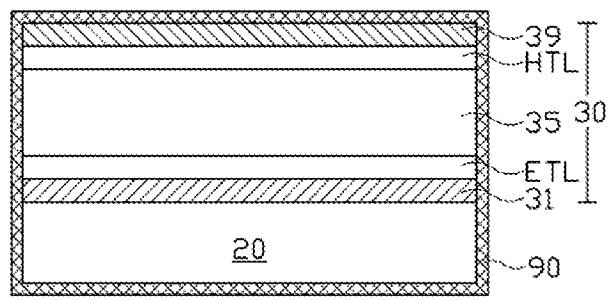
Figure 4:
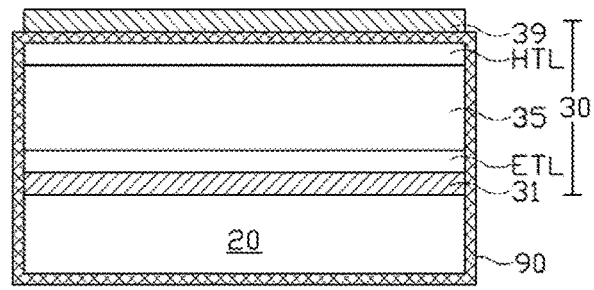

Next, the X-ray detector 10 of FIGS. 3 and 4 is configured such that a photoelectric element 30 having a PIN structure is formed on a substrate 20. The photoelectric element 30 having a PIN structure includes a semiconductor structure between the first and second electrodes 31, 39, the semiconductor structure being composed of an I (intrinsic)-type photoconductor film 35, a P (positive)-type hole transport layer HTL, and an N (negative)-type electron transport layer ETL.

Here, when the first electrode 31 is a cathode and the second electrode 39 is an anode, the electron transport layer ETL is disposed between the photoconductor film 35 and the first electrode 31 and the hole transport layer HTL is disposed between the photoconductor film 35 and the second electrode 39.

The material for forming the electron transport layer ETL may include, for example, any one or a mixture of at least two selected from among Ti oxide, Zn oxide, In oxide, Sn oxide, W oxide, Nb oxide, Mo oxide, Mg oxide, Zr oxide, Sr oxide, Yr oxide, La oxide, V oxide, Al oxide, Y oxide, Sc oxide, Sm oxide, Ga oxide, In oxide, and SrTi oxide, or may include an organic semiconductor such as PCBM. Taking into consideration the processing temperature, Zn oxide or Ti oxide, which is a material having low processing temperature of about room temperature, is preferably used.

The material for forming the hole transport layer HTL may include, for example, any one or a mixture of at least two selected from among thiophene, para-phenylenevinylene, carbazole, and triphenylamine. Taking into consideration energy matching with the perovskite photoconductor film 35, at least one of thiophene and triphenylamine is preferably used, and triphenylamine is more preferably used.

Similarly to FIGS. 1 and 2, the X-ray detector of FIGS. 3 and 4 may include a sealing member 90.

For example, the X-ray detector 10 of FIG. 3 is configured such that the sealing member 90 is provided so as to seal the entire stacking structure comprising the substrate 20 and the photoelectric element 30 from the outside.

In another example, the X-ray detector 10 of FIG. 4 is configured such that the sealing member 90 is provided so as to seal the entire stacking structure comprising the substrate 20 and the construction (i.e. the first electrode 31, and the semiconductor structure comprising the electron transport layer ETL, the photoconductor film 35 and the hole transport layer HTL) of the photoelectric element 30, other than the second electrode 39.

Figure 5:
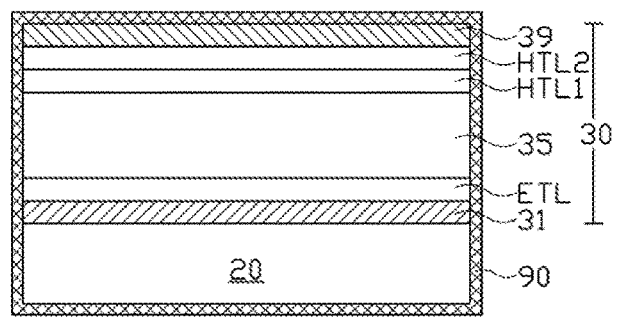
Figure 6:
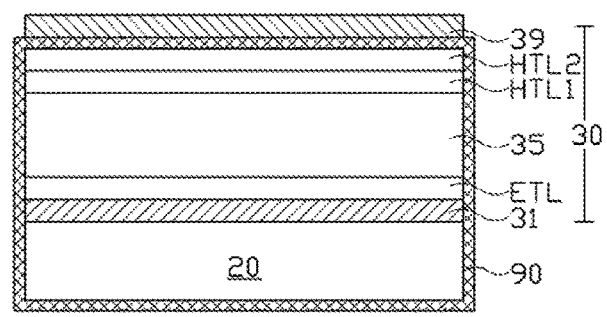

Next, the X-ray detector 10 of FIGS. 5 and 6 is configured such that a photoelectric element 30 having a PPIN structure is formed on a substrate 20. The photoelectric element 30 having a PPIN structure includes a semiconductor structure between the first and second electrodes 31, 39, the semiconductor structure being composed of an I (intrinsic)-type photoconductor film 35, P-type first and second hole transport layers HTL1, HTL2, and an N-type electron transport layer ETL. Here, when the first electrode 31 is a cathode and the second electrode 39 is an anode, the electron transport layer ETL is disposed between the photoconductor film 35 and the first electrode 31, and the first and second hole transport layers HTL1, HTL2 are disposed between the photoconductor film 35 and the second electrode 39. When the X-ray detector 10 of FIGS. 5 and 6 includes the double-structured hole transport layer in this way, hole transport efficiency may be increased.

Similarly to FIGS. 1 and 2, the X-ray detector of FIGS. 5 and 6 may include a sealing member 90.

For example, the X-ray detector 10 of FIG. 5 is configured such that the sealing member 90 is provided so as to seal the entire stacking structure comprising the substrate 20 and the photoelectric element 30 from the outside.

In another example, the X-ray detector 10 of FIG. 6 is configured such that the sealing member 90 is provided so as to seal the entire stacking structure comprising the substrate 20 and the construction (i.e. the first electrode 31, and the semiconductor structure comprising the electron transport layer ETL, the photoconductor film 35 and the first and second hole transport layers HTL1, HTL2) of the photoelectric element 30, other than the second electrode 39.

Figure 7:
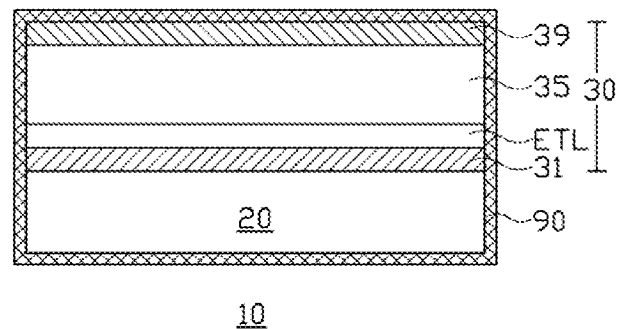
Figure 8:
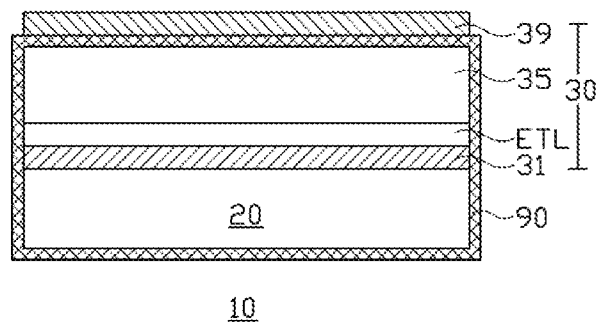

Next, the X-ray detector 10 of FIGS. 7 and 8 is configured such that a photoelectric element 30 having a PN structure is formed on a substrate 20. The photoelectric element 30 having a PN structure includes a semiconductor structure between the first and second electrodes 31, 39, the semiconductor structure being composed of one selected from among a P-type hole transport layer HTL and an N-type electron transport layer ETL and a photoconductor film 35 having a type opposite thereto.

Here, FIGS. 7 and 8 illustrate the case where one transport layer selected from among a P-type hole transport layer HTL and an N-type electron transport layer ETL is positioned at the first electrode 31 and the photoconductor film 35 is formed thereon. Although not shown, in an alternative embodiment, one transport layer selected from among a P-type hole transport layer HTL and an N-type electron transport layer ETL may be positioned at the second electrode 39, and the photoconductor film 35 may be formed thereunder.

Although not shown, in an alternative embodiment, a P-type hole transport layer HTL and an N-type electron transport layer ETL may be provided, one of which may contain the photoconductor in the form of particles, namely photoconductor particles, dispersed therein.

Similarly to FIGS. 1 and 2, the X-ray detector of FIGS. 7 and 8 may include a sealing member 90.

For example, the X-ray detector 10 of FIG. 7 is configured such that the sealing member 90 is provided so as to seal the entire stacking structure comprising the substrate 20 and the photoelectric element 30 from the outside.

In another example, the X-ray detector 10 of FIG. 8 is configured such that the sealing member 90 is provided so as to seal the entire stacking structure comprising the substrate 20 and the construction (i.e. the first electrode 31, and the semiconductor structure comprising the electron transport layer ETL or the hole transport layer HTL and the photoconductor film 35) of the photoelectric element 30, other than the second electrode 39.

Figure 9:
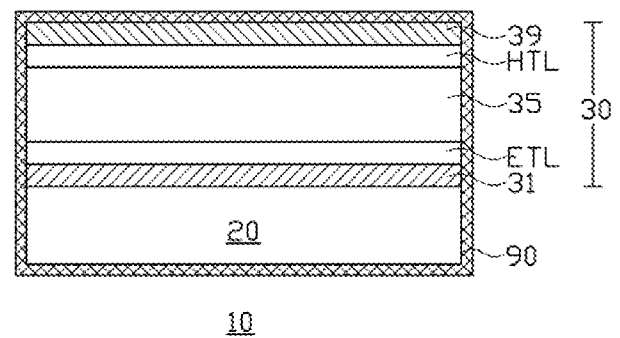
Figure 10:
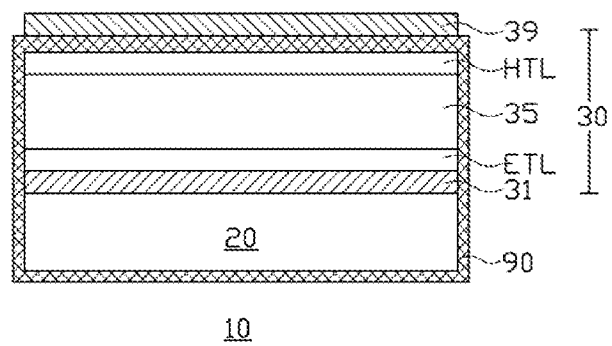

Next, the X-ray detector 10 of FIGS. 9 and 10 is configured such that a photoelectric element 30 having a PPN structure is formed on a substrate 20. The photoelectric element 30 having a PPN structure includes a semiconductor structure between the first and second electrodes 31, 39, the semiconductor structure being composed of a P-type hole transport layer HTL, a P-type photoconductor film 35, and an N-type electron transport layer ETL. As such, the P-type photoconductor film 35 is disposed so as to be adjacent to the electron transport layer ETL.

Although not shown, in an alternative embodiment, in lieu of the P-type photoconductor film 35, a P-type additional hole transport layer may be formed, and the photoconductor in the form of particles, namely photoconductor particles 35a may be provided in the form of being dispersed in the additional hole transport layer.

As described above, the X-ray detector 10 according to the embodiment of the present invention may be variously configured, and the PN junction structure having P-type and N-type semiconductor material layers may also be easily fabricated. Here, the PN junction structure is characterized in that it may effectively reduce a dark current.

The direct-conversion-type X-ray detector as above may be used as an X-ray sensor in various applications in diverse fields, for example, a dental CT or cephalo sensor, a dental panorama sensor, an intraoral sensor, a mammography sensor, a medical fluoroscopy X-ray sensor, etc.

The X-ray output intensity of the X-ray irradiator, i.e. the tube voltage of the X-ray irradiator, required for such a variety of X-ray sensors, is different. Accordingly, taking into account the X-ray absorption efficiency, the thickness range required for the perovskite photoconductor film in these X-ray sensors may also vary.

In this regard, a description is given with reference to [Table 2] to [Table 7] below. [Table 2] to [Table 7] respectively show the results of measurement of X-ray absorption efficiency relative to the thickness of the photoconductor film in a dental CT or cephalo sensor, a dental panorama sensor, an intraoral sensor, a mammography sensor, and a medical fluoroscopy X-ray sensor.

In [Table 2] to [Table 7], the thickness range necessary for the photoconductor film in order to achieve X-ray absorption efficiency of 60% or more in each sensor is as follows:

Dental CT or cephalo sensor: 200 μm~800 μm
Dental panorama sensor: 150 μm~600 μm
I/O (Intraoral) sensor: 100 μm~450 μm
Mammography sensor: 60 μm~300 μm
Medical fluoroscopy X-ray sensor (Mobile C-arm and Mini Mobile C-arm): 90 μm~1000 μm.

TABLE 2

Dental CT & Cephalo (mainly used tube voltage: 90 kVp)/necessary thickness: 200~800 μm

| Thickness (μm) | In | Out | Attenuation | Absorption (%) |
|---|---|---|---|---|
| 100 | 2.65E−05 | 1.59E−05 | 60.09441088 | 39.90558912 |
| 150 | 2.66E−05 | 1.28E−05 | 48.28222013 | 51.71777987 |
| 200 | 2.66E−05 | 1.04E−05 | 39.12373652 | 60.87626348 |
| 250 | 2.67E−05 | 8.55E−06 | 32.05338732 | 67.94661268 |
| 300 | 2.66E−05 | 7.09E−06 | 26.67180451 | 73.32819549 |
| 350 | 2.66E−05 | 6.05E−06 | 22.74398496 | 77.25601504 |
| 400 | 2.66E−05 | 5.18E−06 | 19.47894737 | 80.52105263 |
| 450 | 2.66E−05 | 4.50E−06 | 16.91090226 | 83.08909774 |
| 500 | 2.66E−05 | 3.88E−06 | 14.57293233 | 85.42706767 |
| 550 | 2.66E−05 | 3.42E−06 | 12.85 | 87.15 |

TABLE 3

Panorama (mainly used tube voltage: 75 kVp)/necessary thickness: 150~600 μm

| Thickness (μm) | In | Out | Attenuation | Absorption (%) |
|---|---|---|---|---|
| 100 | 4.89E−05 | 2.65E−05 | 54.10656642 | 45.89343358 |
| 150 | 4.91E−05 | 2.01E−05 | 40.9693244 | 59.0306756 |
| 200 | 4.92E−05 | 1.55E−05 | 31.4683894 | 68.5316106 |
| 250 | 4.93E−05 | 1.22E−05 | 24.69859955 | 75.30140045 |
| 300 | 4.93E−05 | 9.72E−06 | 19.72167563 | 80.27832437 |
| 350 | 4.93E−05 | 7.83E−06 | 15.87666092 | 84.12333908 |
| 400 | 4.93E−05 | 6.44E−06 | 13.05675528 | 86.94324472 |

TABLE 4

I/O sensor (mainly used tube voltage: 60 kVp)/necessary thickness: 100~450 μm

| Thickness (μm) | In | Out | Attenuation | Absorption (%) |
|---|---|---|---|---|
| 80 | 3.16E−05 | 1.55E−05 | 49.00875834 | 50.99124166 |
| 90 | 3.17E−05 | 1.43E−05 | 45.30011683 | 54.69988317 |
| 100 | 3.17E−05 | 1.34E−05 | 42.17422879 | 57.82577121 |
| 110 | 3.17E−05 | 1.24E−05 | 39.03107861 | 60.96892139 |
| 130 | 3.18E−05 | 1.06E−05 | 33.3941893 | 66.6058107 |
| 150 | 3.18E−05 | 9.25E−06 | 29.07752791 | 70.92247209 |
| 200 | 3.18E−05 | 6.59E−06 | 20.72369869 | 79.27630131 |

TABLE 5

Mammo (mainly used tube voltage: 30 kVp)/necessary thickness: 60~300 μm

| Thickness (μm) | In | Out | Attenuation | Absorption (%) |
|---|---|---|---|---|
| 50 | 7.96E−05 | 3.61E−05 | 45.4086058 | 54.5913942 |
| 60 | 2.52E−05 | 9.99E−06 | 39.64057603 | 60.35942397 |
| 70 | 2.52E−05 | 8.64E−06 | 34.27098207 | 65.72901793 |
| 80 | 2.52E−05 | 7.55E−06 | 29.93138188 | 70.06861812 |
| 90 | 2.52E−05 | 6.54E−06 | 25.95605442 | 74.04394558 |
| 100 | 2.52E−05 | 5.72E−06 | 22.68155317 | 77.31844683 |
| 150 | 2.52E−05 | 2.98E−06 | 11.81439619 | 88.18560381 |
| 200 | 2.52E−05 | 1.53E−06 | 6.057421581 | 93.94257842 |

TABLE 6

Mobile C-arm (mainly used tube voltage: 120 kVp)/necessary thickness: 500 μm or more

| Thickness (μm) | In | Out | Attenuation | Absorption (%) |
|---|---|---|---|---|
| 100 | 1.02E−05 | 7.84E−06 | 76.56698915 | 23.43301085 |
| 300 | 1.05E−05 | 5.64E−06 | 53.73809524 | 46.26190476 |
| 350 | 1.06E−05 | 5.24E−06 | 49.70616114 | 50.29383886 |
| 500 | 1.06E−05 | 4.16E−06 | 39.22380458 | 60.77619542 |
| 550 | 1.06E−05 | 3.92E−06 | 36.93490566 | 63.06509434 |
| 600 | 1.06E−05 | 3.72E−06 | 35.10660377 | 65 |
| 650 | 1.06E−05 | 3.51E−06 | 33.11415094 | 67 |
| 700 | 1.06E−05 | 3.23E−06 | 30.36793074 | 69 |
| 750 | 1.06E−05 | 2.98E−06 | 28.00526662 | 71 |

TABLE 7

Mini C-arm (mainly used tube voltage: 65 kVp)/necessary thickness: 90~500 μm

| Thickness (μm) | In | Out | Attenuation | Absorption (%) |
|---|---|---|---|---|
| 80 | 8.16E−05 | 3.49E−05 | 42.79164419 | 57.20835581 |
| 90 | 8.18E−05 | 2.95E−05 | 36.10954816 | 63 |
| 100 | 8.18E−05 | 2.72E−05 | 33.26121237 | 66.73878763 |
| 150 | 8.20E−05 | 1.89E−05 | 23.10337679 | 76.89662321 |
| 200 | 8.21E−05 | 1.35E−05 | 16.466475 | 83.533525 |
| 250 | 8.21E−05 | 9.75E−06 | 11.87029686 | 88.12970314 |
| 300 | 8.21E−05 | 7.26E−06 | 8.842874543 | 91.15712546 |

As described above, the perovskite material of the present embodiment has properties suitable for use as the photoconductor for a direct-conversion-type X-ray detector, and moreover, is inexpensive, exhibits superior deposition properties on a substrate, and is easy to manufacture. Thus, the direct-conversion-type X-ray detector may be mass-produced at low cost within a short processing time.

Second Embodiment

The direct-conversion-type X-ray detector according to a second embodiment of the present invention includes a quantum dot material for converting X-rays having specific energy into visible light, in addition to the perovskite material as the photoconductor.

The perovskite material and the quantum dot material may have different X-ray energy ranges in terms of X-ray absorption efficiency, thus advantageously absorbing X-rays across a wide energy range from substantially low energy to high energy.

The quantum dot material is able to absorb X-rays in the corresponding energy range to thus emit visible light corresponding thereto. The perovskite material is able to absorb X-rays in the corresponding energy range to thus directly produce electron-hole pairs and also to absorb visible light emitted from the quantum dot material to thus produce electron-hole pairs therefor.

In this way, the X-ray detector of the present embodiment is responsible for a photoelectric conversion function for converting incident X-rays into an electrical signal using two materials together, and specifically, may directly convert X-rays into an electrical signal and also convert visible light emitted through the quantum dot material into an electrical signal. Accordingly, the X-ray detector of the present embodiment may be referred to as a hybrid-type X-ray detector in which the direct conversion type is combined with an indirect conversion type.

Hereinafter, a detailed description is given of the hybrid-type X-ray detector.

Perovskite, having a crystal structure represented by the chemical formula ABX3, is known to be a special material that exhibits the properties of all of a non-conductor, a semiconductor, a conductor, and even a superconductor. In this embodiment, such a perovskite material is used as the photoconductor.

Here, the perovskite material used in the present embodiment is specified, and the materials that constitute ABX3 are as follows.

A: an organic material, examples of which include methyl ammonium ($CH_3NH_3$) and formamidinium ($NH_2CH=NH_2$), or an inorganic material, an example of which includes cesium (Cs);

B: a metal material, examples of which include divalent transition metals, such as Pb, Sn, Cu, Ni, Bi, Co, Fe, Mn, Cr, Cd, Ge, Yb, and the like;

X: a halogen material, examples of which include $I_x Br_{(1-x)}$, $I_x Cl_{(1-x)}$, and $Br_x Cl_{(1-x)}$ ($0.2 \leq x \leq 1$, a real number).

In the present embodiment, when the perovskite material having the above structure is used, a photoconductor having superior properties may be obtained.

Here, among the examples of the B material that is listed above, Pb, Bi and Cd are more preferably used than the other materials.

Below is a description of the perovskite material using an organic material as the A material.

[Table 8] below shows the properties of $(CH_3NH_3)PbI_3$, which is an example of the perovskite material using an organic material as the A material, and of existing proposed materials.

With reference thereto, the perovskite material of the present embodiment has a high atomic number, low energy band gap and low ionization energy, and may exhibit increased quantum efficiency due to the small trap density. It has higher mobility properties than a-Se, which is currently widely used for direct-conversion-type detectors.

TABLE 8

|  | Photoconductor | | | | | |
| --- | --- | --- | --- | --- | --- | --- |
|  | a-Se | CdTe | Poly-$HgI_2$ | Poly-$PbI_2$ | Poly-PbO | Poly-$(CH_3NH_3)PbI_3$ |
| Atomic number (Z) | 34 | 48/62 | 80/53 | 82/53 | 82/8 | 82/53 |
| Energy band gap (eV) | 2.2 | 1.44 | 2.1 | 2.4 | 1.9 | 1.55 |
| Density (g/cm$^3$) | 4.3 | 5.85 | 6.36 | 6.16 | 9.6 | 4.28 |
| Trap density (cm$^{-3}$) | $10^{16}$ | $10^{13}$~$10^{14}$ | ~$10^{13}$ | ~$10^{13}$ | — | ~$10^{10}$ |
| Ionization energy (W±) | 45 | 5 | 5 | 5 | 8 | <5 |
| Mobility (cm$^2$/Vs) Electron | ~$10^{-3}$ | $10^3$ | $10^2$ | — | 50 | ~6 |
| Mobility (cm$^2$/Vs) Hole | ~$10^{-2}$ | ~90 | 4 | 0.01~0.1 | — | 19 |
| Resistivity (Ω) | $10^{14}$~$10^{15}$ | $10^9$ | ~$10^{13}$ | $10^{11}$~$10^{12}$ | ~$10^{12}$ | $10^7$ |

As mentioned above, the perovskite material of the present embodiment may sufficiently satisfy requirements through the preparation of $CH_3NH_3Pb(I_x Br_{1-x})_3$.

Furthermore, the perovskite material using the organic material as the A material is inexpensive compared to existing materials, and may be easily formed through synthesis of organic or inorganic materials, and thus enables the mass production of a large-area detector at low cost within a short time.

The perovskite material using the organic material as the A material may exhibit superior deposition ability on a substrate compared to existing materials, to thus improve interfacial characteristics with a CMOS substrate or the like, thereby improving the detection efficiency of the detector.

In the perovskite material using the organic material as the A material, the crystal size of perovskite is determined depending on the concentration. Specifically, the crystal size decreases with an increase in the concentration of the organic material, and increases with a decrease in the concentration of the organic material. The crystal size is related to the amount of absorption of X-rays, and specifically the amount of absorption of X-rays is increased with a decrease in the crystal size. Based on the results of measurement of light absorbance through the control of the concentration of the organic material, light absorbance becomes optimized when the concentration of the organic material is 35 mM~45 mM, and preferably 38 mM, as in solar light.

The perovskite material, which is used as the photoconductor for a direct-conversion-type X-ray detector, has to be formed into a relatively thick film having a predetermined thickness or more, taking into consideration the X-ray absorption properties, and is preferably provided in the form of a film having a thickness ranging from 100 µm to at least 1 mm.

Such a photoconductor may be manufactured using a spray-coating process, a sol-gel-coating process, a spin-coating process, a slot-die-coating process, a thermal deposition process, a sequential vapor deposition process, a vapor-assisted solution process, etc.

Among these, a spray-coating process, a sol-gel-coating process, a vapor deposition process or a vapor-assisted solution process is preferably performed.

Here, the vapor deposition process may be performed in various manners, and, for example, may be a thermal deposition process. The thermal deposition process is able to form a uniform thick film having good quality compared to the other deposition processes, and impurity doping in the air may be maximally suppressed.

The quantum dot material functions to mainly absorb X-rays having relatively low energy in terms of X-ray absorption efficiency, compared to the perovskite material.

Examples of the quantum dot material may include a-Se, Cs, CdSe, CdS, PbO, and $PbI_2$.

The quantum dot preferably has a diameter of about 1 nm~100 nm. When the quantum dot material is provided in the form of a film, the thickness of the quantum dot film preferably falls in the range of about 100 nm~1000 µm.

Hereinafter, various examples of the hybrid-type X-ray detector using the perovskite material and the quantum dot material according to the present embodiment are described with reference to the drawings.

FIGS. 11 to 22 are cross-sectional views schematically showing various structures of a hybrid-type X-ray detector using a perovskite material and a quantum dot material according to a second embodiment of the present invention.

The X-ray detector 110 of FIGS. 11 to 14 includes a photoelectric element 130 having a Schottky structure on a substrate 120.

The substrate 120 includes a plurality of detection pixels for reading an electric signal generated from the photoelectric element. The substrate 120 is provided in various forms, and examples thereof may include a CMOS substrate, a glass substrate, a plastic substrate having flexible properties, etc. Here, examples of the plastic substrate may include polyethylene terephthalate (PET), polyethylene naphthalate (PEN), polyimide (PI), polycarbonate (PC), polypropylene (PP), triacetyl cellulose (TAC), and polyether sulfone (PES).

The photoelectric element 130 includes a first electrode 131, which is the lower electrode formed on the substrate 120, a second electrode 139, which is the upper electrode formed on the first electrode 131, and a semiconductor structure disposed between the first and second electrodes 131, 139 to perform a photoelectric function, the semiconductor structure being composed of a photoconductor film 135 formed of a perovskite material and a quantum dot material.

The quantum dot material may be provided in various forms, for example, in the forms depicted in FIGS. 11, 12, 13, and 14.

Figure 11:
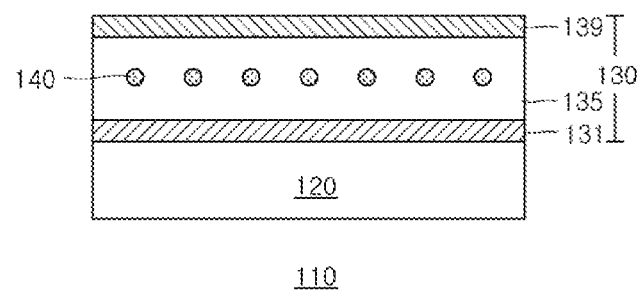
FIGS. 11 to 22 are cross-sectional views schematically showing various structures of a hybrid-type X-ray detector using a perovskite material and a quantum dot material according to a second embodiment of the present invention.

In this regard, with reference to FIG. 11, a quantum dot 140 in the form of particles may be provided in the form of being dispersed in the photoconductor film 35.

Figure 12:
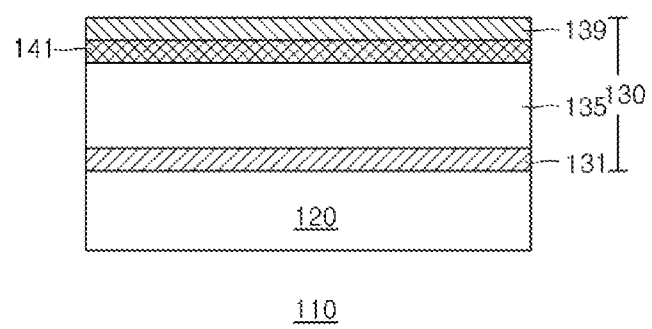
Figure 13:
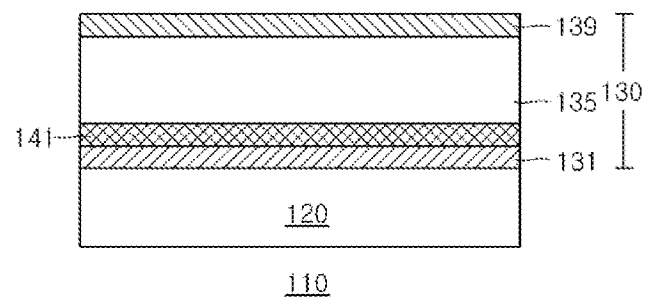
Figure 14:
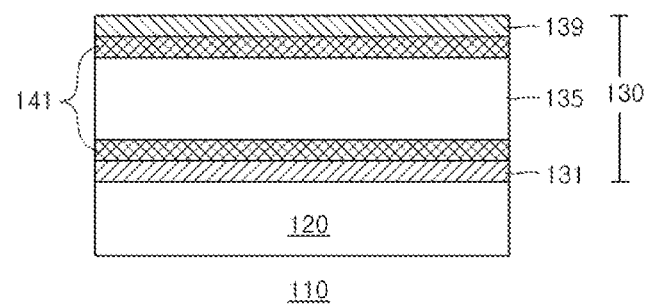

Also, with reference to FIG. 12, 13, or 14, a quantum dot film 141 is formed, and may be disposed so as to come into direct contact with either or both of the upper surface and the lower surface of the photoconductor film 135.

The material for forming the first and second electrodes 131, 139 may include, for example, any one or a mixture of at least two selected from among ITO, F—SnO, gold, silver, platinum, palladium, copper, aluminum, carbon, cobalt sulfide, copper sulfide, and nickel oxide, or alternatively may include an inorganic conductive electrode material, such as single or multiple carbon nanotubes or graphene, an organic conductive electrode material such as PEDOT:PSS, or a nanowire electrode material such as a silver nanowire (Ag Nanowire) metal material.

When the first electrode 131 and the photoconductor film 135 come into direct contact with each other, an adhesive polymer may be provided therebetween, and the adhesive polymer may be formed with PAP (polyacryloyl piperidine).

Next, the X-ray detector 110 of FIGS. 15 to 18 is configured such that a photoelectric element 130 having a PIN structure is formed on a substrate 120. The photoelectric element 130 having a PIN structure includes a semiconductor structure between the first and second electrodes 131, 139, the semiconductor structure being composed of an I (intrinsic)-type photoconductor film 135, a P (positive)-type hole transport layer HTL, and an N (negative)-type electron transport layer ETL, as well as the semiconductor structure including a quantum dot material.

Here, the quantum dot material may be provided in various forms, for example, in the forms depicted in FIGS. 15 to 18, like FIGS. 11 to 14.

Figure 15:
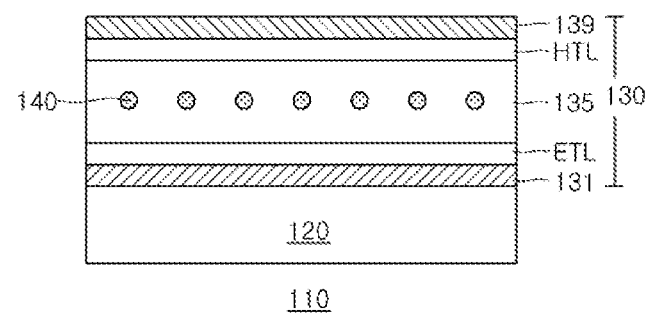

For example, with reference to FIG. 15, a quantum dot 140 may be provided in the form of being dispersed in the photoconductor film 135.

Figure 16:
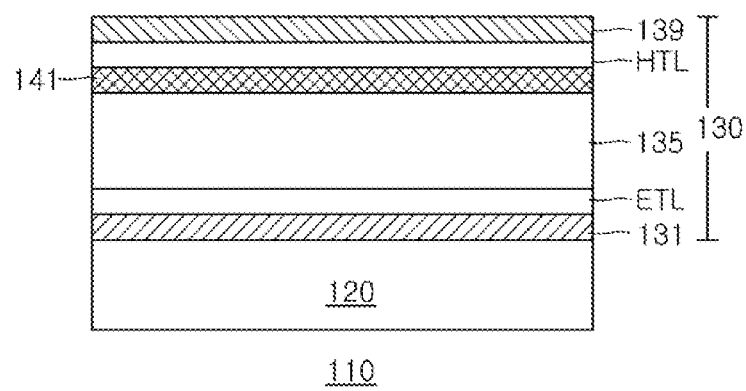
Figure 17:
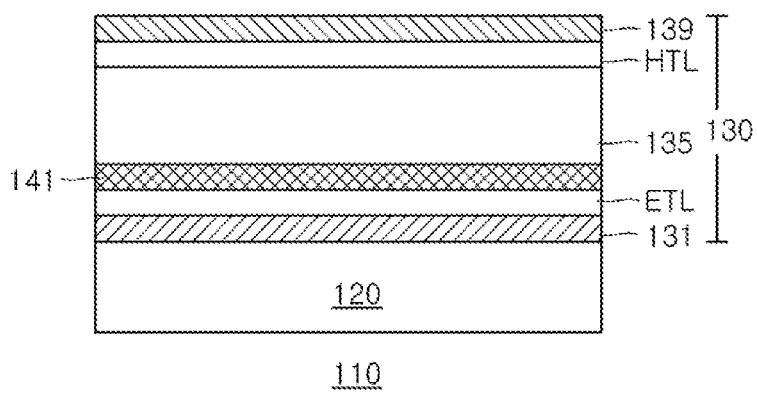
Figure 18:
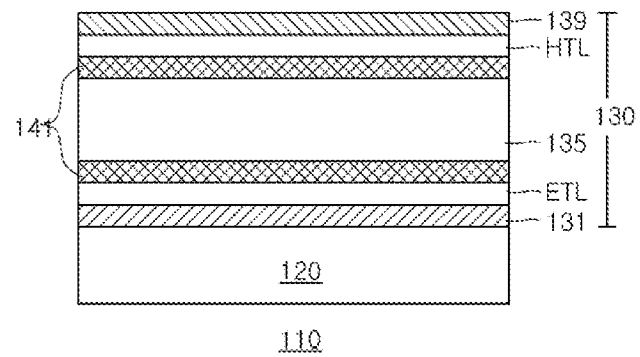

In another example, with reference to FIG. 16, 17, or 18, a quantum dot film 141 is formed, and may be disposed so as to come into direct contact with either or both of the upper surface and the lower surface of the photoconductor film 135.

Here, when the first electrode 131 is a cathode and the second electrode 139 is an anode, the electron transport layer ETL is disposed at the first electrode 131 and the hole transport layer HTL is disposed at the second electrode 139.

The material for forming the electron transport layer ETL may include, for example, any one or a mixture of at least two selected from among Ti oxide, Zn oxide, In oxide, Sn oxide, W oxide, Nb oxide, Mo oxide, Mg oxide, Zr oxide, Sr oxide, Yr oxide, La oxide, V oxide, Al oxide, Y oxide, Sc oxide, Sm oxide, Ga oxide, In oxide, and SrTi oxide, or may include an organic semiconductor such as PCBM. As such, Zn oxide or Ti oxide is preferably used.

The material for forming the hole transport layer HTL may include, for example, any one or a mixture of at least two selected from among thiophene, para-phenylenevinylene, carbazole, and triphenylamine. Taking into consideration energy matching with the perovskite photoconductor film 135, at least one of thiophene and triphenylamine is preferably used, and triphenylamine is more preferably used.

Next, the X-ray detector 110 of FIGS. 19 to 22 is configured such that a photoelectric element 130 having a PN structure is formed on a substrate 120. The photoelectric element 130 having a PN structure includes a semiconductor structure between the first and second electrodes 131, 139, the semiconductor structure being composed of one selected from among a P-type hole transport layer HTL and an N-type electron transport layer ETL and a photoconductor film 135 having a type opposite thereto, as well as the semiconductor structure including a quantum dot material.

The disposition relation of the P-type semiconductor film and the N-type semiconductor film in the semiconductor structure is determined depending on whether the first or second electrode 131, 139 functions as either the anode or the cathode.

FIGS. 19 to 22 illustrate the case where one transport layer selected from among a P-type hole transport layer HTL and an N-type electron transport layer ETL is positioned at the first electrode 131 and the photoconductor film 135 is formed thereon. Although not shown, in an alternative embodiment, one transport layer selected from among a P-type hole transport layer HTL and an N-type electron transport layer ETL may be positioned at the second electrode 139, and the photoconductor film 135 may be formed thereunder.

Here, the quantum dot material may be provided in various forms, for example, in the forms depicted in FIGS. 19 to 22, like FIGS. 11 to 14.

Figure 19:
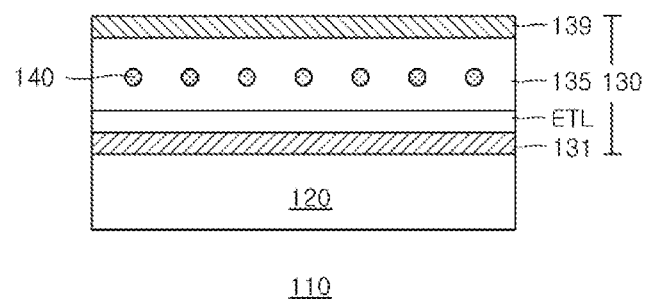

For example, with reference to FIG. 19, a quantum dot 140 may be provided in the form of being dispersed in the photoconductor film 135.

Figure 20:
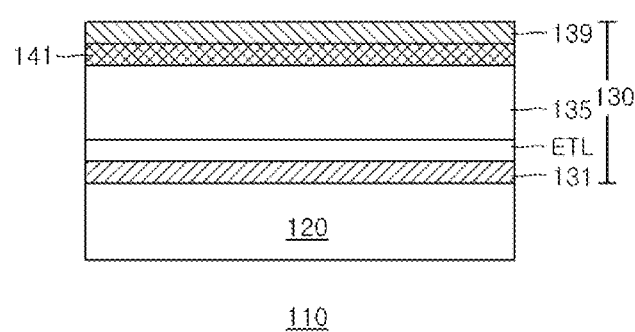
Figure 21:
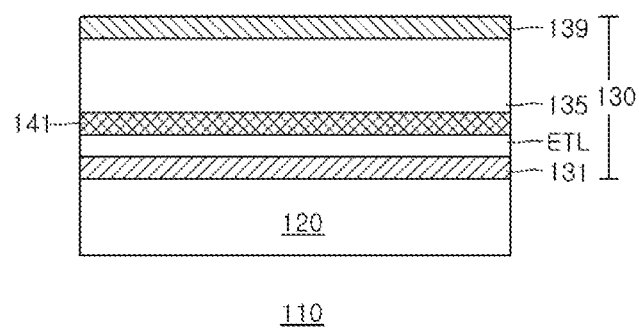
Figure 22:
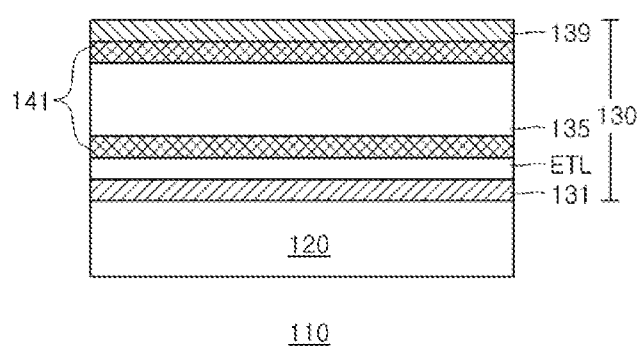

In another example, with reference to FIG. 20, 21, or 22, a quantum dot film 141 is formed, and may be disposed so as to come into direct contact with either or both of the upper surface and the lower surface of the photoconductor film 135.

As described hereinbefore, the perovskite material of the present embodiment has properties suitable for use as a photoconductor for an X-ray detector, and moreover, is inexpensive, can exhibit superior deposition properties on a substrate, and is easy to manufacture. Thus, an X-ray detector can be mass-produced at low cost within a short processing time.

In addition to the perovskite material, a quantum dot material for converting X-rays having specific energy into visible light is used. Accordingly, an X-ray detector, which is capable of absorbing X-rays in a wide energy range from substantially low energy to high energy and thus has high resolution and low noise, can be manufactured.

The invention claimed is:

1. An X-ray detector, comprising:
   a first electrode on a substrate;
   a semiconductor structure including a photoconductor using a perovskite material on the first electrode; and
   a second electrode on the semiconductor structure,
   wherein the substrate is a CMOS substrate or a plastic substrate, and an adhesive polymer formed between the first electrode and the photoconductor is further included.

2. The X-ray detector of claim 1, wherein the perovskite material is represented by a chemical formula ABX3, A being Cs, methyl ammonium ($CH_3NH_3$) or formamidinium ($NH_2CH=NH_2$), B being Pb, Sn, Cu, Ni, Bi, Co, Fe, Mn, Cr, Cd, Ge, or Yb, and X being $I_xBr_{(1-x)}$, $I_xCl_{(1-x)}$, or $Br_xCl_{(1-x)}$ ($0.2 \leq x \leq 1$, a real number).

3. The X-ray detector of claim 1, wherein the semiconductor structure includes a hole transport layer and an electron transport layer, and the photoconductor is provided in a film form between the hole transport layer and the electron transport layer.

4. The X-ray detector of claim 3, wherein the hole transport layer includes first and second hole transport layers.

5. The X-ray detector of claim 1, wherein the semiconductor structure includes one of an electron transport layer and a hole transport layer and a photoconductor film having a type opposite thereto and configured such that the photoconductor is provided in a film form, or includes an electron transport layer and a hole transport layer, and when the semiconductor structure includes the electron transport layer and the hole transport layer, the photoconductor is provided in a form of particles inside one of the electron transport layer and the hole transport layer.

6. The X-ray detector of claim 1, wherein the semiconductor structure includes a hole transport layer and an electron transport layer, with a photoconductor film having a P type disposed therebetween and configured such that the photoconductor is provided in a film form, or includes a hole transport layer and an electron transport layer, with an additional hole transport layer disposed therebetween and configured such that the photoconductor is provided in a form of particles therein.

7. The X-ray detector of claim 1, wherein the adhesive polymer is PAP (polyacryloyl piperidine).

8. The X-ray detector of claim 1, further comprising a sealing member configured to seal an entire stacking structure comprising the substrate, the first electrode, the semiconductor structure and the second electrode, or to seal an entire stacking structure comprising the substrate, the first electrode and the semiconductor structure.

9. The X-ray detector of claim 8, wherein the sealing member is formed of any one or a mixture of at least two selected from among a polyethylene-based resin, a polypropylene-based resin, a cyclic polyolefin-based resin, a polystyrene-based resin, an acrylonitrile-styrene copolymer, an acrylonitrile-butadiene-styrene copolymer, a poly(vinyl chloride)-based resin, a fluorine-based resin, a poly(meth) acrylate-based resin, and a polycarbonate-based resin, or is formed of Parylene.

10. The X-ray detector of claim 1, wherein a film of the photoconductor has a thickness of 200 μm~800 μm when the X-ray detector is used for at least one of a dental CT sensor and a cephalo sensor, a thickness of 150 μm~600 μm when the X-ray detector is used for a dental panorama sensor, a thickness of 100 μm~450 μm when the X-ray detector is used for an intraoral (I/O) sensor, a thickness of 60 μm~300 μm when the X-ray detector is used for a mammography sensor, and a thickness of 90 μm~1000 μm when the X-ray detector is used for a medical fluoroscopy X-ray sensor.

11. The X-ray detector of claim 1, wherein the semiconductor structure includes a photoconductor film using the perovskite material and a quantum dot material for converting incident X-rays into visible light.

12. The X-ray detector of claim 11, wherein the quantum dot is a-Se, Cs, CdSe, CdS, PbO, or $PbI_2$, and has a diameter of 1 nm~100 nm.

13. The X-ray detector of claim 11, wherein the quantum dot is provided in a form of being dispersed in the photoconductor film, or in a form of a film in contact with at least one of an upper surface and a lower surface of the photoconductor film.

14. The X-ray detector of claim 13, wherein the semiconductor structure includes one of a hole transport layer and an electron transport layer, and one of the hole transport layer and the electron transport layer is disposed between one of the first and second electrodes and the photoconductor film configured such that the quantum dot is provided therein or thereon.

15. The X-ray detector of claim 13, wherein the semiconductor structure includes a hole transport layer and an electron transport layer, the hole transport layer is disposed between one of the first and second electrodes and the photoconductor film configured such that the quantum dot is provided therein or thereon, and the electron transport layer is disposed between a remaining one of the first and second electrodes and the photoconductor film configured such that the quantum dot is provided therein or thereon.

16. The X-ray detector of claim 13, wherein the film comprising the quantum dot has a thickness of 100 nm~1000 μm.

* * * * *